United States Patent [19]

DeWald

[11] Patent Number: 4,469,868

[45] Date of Patent: Sep. 4, 1984

[54] ALKYLIMIDAZO[1,2-C]PYRAZOLO[3,4-E]PYRIMIDINES

[75] Inventor: Horace A. DeWald, Ann Arbor, Mich.

[73] Assignee: Warner-Lambert Company, Morris Plains, N.J.

[21] Appl. No.: 381,484

[22] Filed: May 24, 1982

[51] Int. Cl.³ .................. C07D 487/14; A61K 31/305
[52] U.S. Cl. ..................................... 544/251; 424/251
[58] Field of Search ................. 544/251, 250; 424/251

[56] References Cited

U.S. PATENT DOCUMENTS

| | | | |
|---|---|---|---|
| 3,313,815 | 4/1967 | Wolfe et al. | 544/250 |
| 3,594,379 | 7/1971 | Hardtmann et al. | 544/250 |
| 3,810,894 | 5/1974 | Kranz et al. | 544/250 X |
| 3,887,566 | 6/1975 | Rodway et al. | 544/252 X |
| 3,984,556 | 10/1976 | Hardtmann | 424/251 |
| 4,183,932 | 1/1980 | Yamamoto et al. | 424/251 |
| 4,192,803 | 3/1980 | Wright, Jr. et al. | 260/243.3 |
| 4,206,123 | 6/1980 | McCall | 549/23 |
| 4,230,707 | 10/1980 | Tinney et al. | 424/251 |
| 4,247,553 | 1/1981 | McCall | 424/250 |
| 4,250,181 | 2/1981 | McCall | 424/250 |
| 4,303,660 | 12/1981 | Berenyi | 424/251 |
| 4,337,198 | 6/1982 | Sorg et al. | 260/243.3 |
| 4,352,811 | 10/1982 | Strupczewski et al. | 424/267 |
| 4,358,456 | 11/1982 | Ward | 424/267 |
| 4,374,245 | 2/1983 | Davis et al. | 546/20 |
| 4,379,160 | 4/1983 | Harfenist et al. | 424/274 |
| 4,390,544 | 6/1983 | Davis et al. | 424/267 |
| 4,396,770 | 8/1983 | Davis et al. | 546/198 |
| 4,409,230 | 10/1983 | Davis et al. | 424/267 |
| 4,415,581 | 11/1983 | Davis et al. | 424/267 |
| 5,352,805 | 10/1982 | McCall | 424/250 |

FOREIGN PATENT DOCUMENTS

| | | | |
|---|---|---|---|
| 51-6993 | 1/1976 | Japan | 544/251 |
| 1042299 | 9/1966 | United Kingdom | 544/250 |

OTHER PUBLICATIONS

Clody, et al., Predictability in Psychopharmacology: Preclinical and Clinical Correlations, Sudilovsky, et al., ed., Raven Press, N.Y., (1975), pp. 213–224.

Goodman, et al., The Pharmacological Basis of Therapeutics, 6th ed., MacMillan Publishing Co., N.Y., (1980), p. 392.

Bowie, et al., J. Chem. Soc. Perkin Trans. I, pp. 1106–1107, (1972).

Hardtmann, et al., J. Org. Chem., vol. 39, No. 24, pp. 3599–3600, (1974).

*Primary Examiner*—Donald G. Daus
*Assistant Examiner*—Diana G. Rivers
*Attorney, Agent, or Firm*—Jerry F. Janssen

[57] ABSTRACT

Alkylimidazo[1,2-c]pyrazolo[3,4-e]pyrimidines and pharmaceutically acceptable salts are described. These compounds are antipsychotic agents. Methods for their preparation, pharmaceutical compositions which contain them and methods for using said compositions are also described.

27 Claims, No Drawings

ALKYLIMIDAZO[1,2-c]PYRAZOLO[3,4-e]PYRIMIDINES

BACKGROUND OF THE INVENTION

The compounds of the invention, imidazo[1,2-c]pyrazolo[3,4-e]pyrimidines are structurally novel class of compounds. J. Chem. Soc., Perkin Trans., I (9) 2387 (1981) discloses a group of nucleosides, certain of which contain an imidazo[1,2-c]pyrazolo[4,3-e]pyrimidine ring system.

SUMMARY OF THE INVENTION

The invention sought to be patented in its generic chemical compound aspect is a compound having the structural formula I

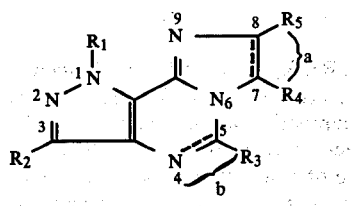

wherein the dashed lines "a" and "b" represent optional double bonds, provided that "a" is not a double bond when "b" is not a double bond; $R_1$, $R_2$, $R_3$, $R_4$, and $R_5$ are H, alkyl of from one to six carbon atoms, or fluorinated alkyl of from one to three carbon atoms; when "a" represents a single bond, $R_4$ may be H/H and $R_5$ is dialkyl each of from one to six carbon atoms or $R_5$ may be H/H and $R_4$ is dialkyl each of from one to six carbon atoms; and the pharmaceutically acceptable salts thereof.

The invention sought to be patented in its first subgeneric chemical compound aspect is a compound having the structural formula Ia

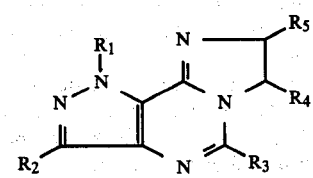

wherein $R_1$, $R_2$, $R_3$, $R_4$, and $R_5$ are H, alkyl of from one to six carbon atoms, or fluorinated alkyl of from one to three carbon atoms; $R_4$ may be H/H and $R_5$ is dialkyl each of from one to six carbon atoms or $R_5$ may be H/H and $R_4$ is dialkyl each of from one to six carbon atoms; and the pharmaceutically acceptable salts thereof.

The invention sought to be patented in its second subgeneric chemical compound aspect is a compound having the structural formula Ib

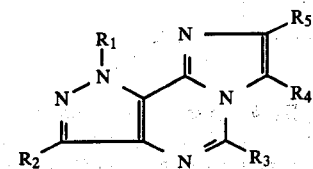

wherein $R_1$, $R_2$, $R_3$, $R_4$, and $R_5$ are H, alkyl of from one to six carbon atoms, or fluorinated alkyl of from one to three carbon atoms; and the pharmaceutically acceptable salts thereof.

The invention sought to be patented in its third subgeneric chemical compound aspect is a compound having the structural formula Ic

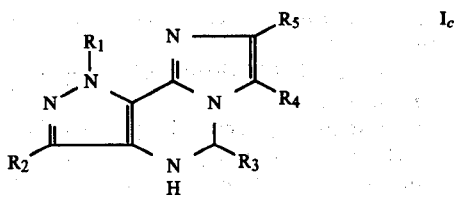

wherein $R_1$, $R_2$, $R_3$, $R_4$, and $R_5$ are H, alkyl of from one to six carbon atoms, or fluorinated alkyl of from one to three carbon atoms; $R_4$ may be H/H and $R_5$ is dialkyl of from one to six carbon atoms or $R_5$ may be H/H and $R_4$ is dialkyl each of from one to six carbon atoms; and the pharmaceutically acceptable salts thereof.

The invention sought to be patented as species of its generic chemical compound aspect are the compounds having the following names:

7,8-dihydro-1,3-dimethyl-1H-imidazo[1,2-c]pyrazolo[3,4-e]pyrimidine;

7,8-dihydro-1,3,8-trimethyl-1H-imidazo[1,2-c]pyrazolo[3,4-e]pyrimidine;

7,8-dihydro-1,3,5,8-tetramethyl-1H-imidazo[1,2-c]pyrazolo[3,4-e]pyrimidine;

7,8-dihydro-1,3,5,8-tetramethyl-1H-imidazo[1,2-c]pyrazolo[3,4-e]pyrimidine (S-form);

7,8-dihydro-1,3,5-trimethyl-1H-imidazo[1,2-c]pyrazolo[3,4-e]pyrimidine (R-form);

7,8-dihydro-1,3,5,7,8-pentamethyl-1H-imidazo[1,2-c]pyrazolo[3,4-e]pyrimidine;

8-ethyl-7,8-dihydro-1,3,5-trimethyl-1H-imidazo[1,2-c]pyrazolo[3,4-e]pyrimidine;

7,8-dihydro-8-isopropyl-1,3,5-trimethyl-1H-imidazo[1,2-c]pyrazolo[3,4-e]pyrimidine dihydrochloride (S-form);

7,8-dihydro-1,3,5,7,7-pentamethyl-1H-imidazo[1,2-c]pyrazolo[3,4-e]pyrimidine;

7,8-dihydro-1,3,5,8,8-pentamethyl-1H-imidazo[1,2-c]pyrazolo[3,4-e]pyrimidine;

5-ethyl-7,8-dihydro-1,3-dimethyl-1H-imidazo[1,2-c]pyrazolo[3,4-e]pyrimidine;

7,8-dihydro-5-ethyl-1,3,8-trimethyl-1H-imidazo[1,2-c]pyrazolo[3,4-e]pyrimidine;

7,8-dihydro-5-ethyl-1,3,7-trimethyl-1H-imidazo[1,2-c]pyrazolo[3,4-e]pyrimidine;

5-cyclopropyl-7,8-dihydro-1,3,8-trimethyl-1H-imidazo[1,2-c]pyrazolo[3,4-e]pyrimidine;

7,8-dihydro-5-isopropyl-1,3,8-trimethyl-1H-imidazo[1,2-c]pyrazolo[3,4-e]pyrimidine;

1-ethyl-7,8-dihydro-3,5-dimethyl-1H-imidazo[1,2-c]pyrazolo[3,4-e]pyrimidine;

7,8-dihydro-1-ethyl-3,5-dimethyl-1H-imidazo[1,2-c]pyrazolo[3,4-e]pyrimidine;

7,8-dihydro-1-ethyl-3,5,8-trimethyl-1H-imidazo[1,2-c]pyrazolo[3,4-e]pyrimidine;

1,5-diethyl-7,8-dihydro-3,8-dimethyl-1H-imidazo[1,2-c]pyrazolo[3,4-e]pyrimidine;

7,8-dihydro-3,5,8-trimethyl-1-n-propyl-1H-imidazo[1,2-c]pyrazolo[3,4-e]pyrimidine;

7,8-dihydro-3,5,8-trimethyl-1-(2,2,2-trifluoroethyl)-1H-imidazo[1,2-c]pyrazolo[3,4-e]pyrimidine;

1,3,5,8-tetramethyl-1H-imidazo[1,2-c]pyrazolo[3,4-e]pyrimidine;

1,3,5,',8-pentamethyl-1H-imidazo[1,2-c]pyrazolo[3,4-e]pyrimidine;

5,6,7,8-tetrahydro-5-ethyl-1,3,8-trimethyl-1H-imidazo[1,2-c]pyrazolo[3,4-e]pyrimidine;

5-ethyl-1,3,8-trimethyl-1H-imidazo[1,2-c]pyrazolo[3,4-e]pyrimidine;

1,3,5,8-tetramethyl-1H-imidazo[1,2-c]pyrazolo[3,4-e]pyrimidine.

The invention sought to be patented in its first generic chemical process aspect is a process for preparing a compound having the structural formula Ia which comprises treating a compound having the structural formula V with an anion chosen from iodide and azide.

The invention sought to be patented in its second generic chemical process aspect is a process for preparing a compound having the structural formula Ia which comprises treating a compound having the structural formula VIII with an orthoester.

The invention sought to be patented in its third generic chemical process aspect is a process for preparing a compound having the structural formula Ia which comprises treating a compound having the structural formula VI with an inorganic halogenating agent.

The invention sought to be patented in its fourth generic chemical process aspect is a process for preparing a compound having the structural formula Ib which comprises treating a compound having the structural formula XVI with an acid.

The invention sought to be patented in its fifth generic chemical process aspect is a process for preparing a compound having the structural formula Ic which comprises treating a compound having the structural formula VIII with an aldehyde.

The invention sought to be patented in its generic pharmaceutical composition aspect is a composition useful for treating psychoses in a mammal consisting essentially of a compound having the structural formula I or mixtures thereof in combination with a pharmaceutically acceptable carrier.

The invention sought to be patented in its pharmaceutical method aspect is a method for treating psychoses in a mammal in need of such treatment; which comprises administering an effective amount of the above defined pharmaceutical composition to said mammal.

DESCRIPTION OF THE PREFERRED EMBODIMENTS

The compounds of the invention having structural formula I wherein "a" represents a single bond and "b" represents a double bond, compounds Ia, may be prepared by several procedures which are considered equivalent for purposes of the invention. A convenient starting material for these procedures is the substituted 7-halo-1H-pyrazolo[4,3-d]pyrimidine having structural formula IV

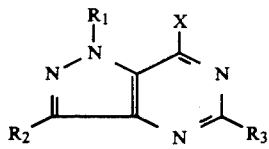

IV wherein $R_1$, $R_2$, and $R_3$ are defined above, and X is chlorine or bromine; preferably chlorine.

The compound having structural formula IV may be treated with an ethyleneimine having the formula

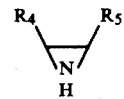

to produce a compound having the structural formula V

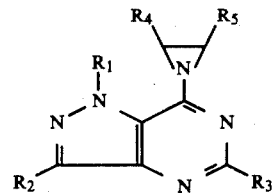

V wherein $R_1$, $R_2$, $R_3$, $R_4$, and $R_5$ are defined above. This reaction is conveniently performed at room temperature in a nonreactive solvent such as a chlorinated alkane, an ether, an aromatic hydrocarbon, and the like in the presence of a hydrogen halide acceptor such as a trialkylamine, pyridine, a metal carbonate or bicarbonate, and the like. In the preferred process compound IV is dissolved in methylene chloride and treated with a slight molar excess of triethylamine, the ethyleneimine is added and the mixture is stirred until the reaction is substantially complete. The reaction is usually allowed to proceed for from about 8 to about 40 hours and may be monitored by, for example thin layer chromatography. The product, V, is isolated and purified by standard procedures.

The compound having formula V is then treated with an anion such as iodide or azide to produce the compound of formula I wherein "a" is a single bond and "b" is a double bond. This reaction is performed in a convenient nonreactive solvent such as a ketone, dimethylsulfoxide, a N,N-dialkylacetamide and the like at an elevated temperature. In the preferred process, the compound having structural formula V is dissolved in acetone and treated with sodium iodide at reflux temperature. The product is then isolated and purified by standard procedures, for example the solvent may be evaporated and the residue may be partitioned between methylene chloride and dilute base. The organic layer is then separated, dried, evaporated, and the residue is recrystallized.

In an alternate procedure, the compound of structural formula IV may be treated with a substituted 2-aminoethanol having the formula $H_2NCHR_5CHR_4OH$ to produce a compound having structural formula VI

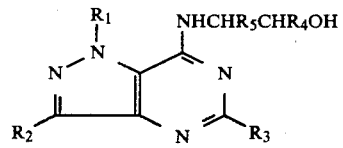

VI wherein $R_1$, $R_2$, $R_3$, $R_4$, and $R_5$ are defined above. This reaction is carried out substantially as described above for the reaction between compound IV and the substituted ethyleneimine. The reaction between IV and certain aminoalcohols may be aided by heating, for example on the steam bath. The choice of the proper reaction variables is within the skill of the art. Compound VI is cyclized to the product of formula I wherein "a" is a single bond and "b" is a double bond by treatment with, for example phosphorous oxychloride at reflux temperature. After evaporation of the phosphorous oxychloride, compound I is isolated and purified by standard procedures substantially as described above.

Compound VI may also be prepared by the reduction of a compound having the structural formula VII

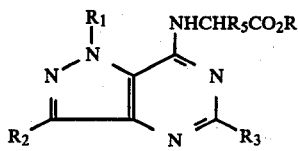

wherein $R_1$, $R_2$, $R_3$, and $R_5$ are defined above and R is any alkyl group. Compound VII is prepared from compound IV by treatment with an amino acid ester having the formula $H_2NCHR_5CO_2R$. This reaction is performed substantially as described above for the reaction between compound IV and the aminoalcohol. Compound VII may be reduced to compound VI by a variety of procedures. The preferred procedure utilizes sodium borohydride in refluxing 95% ethanol. This procedure will produce compounds VI, wherein $R_4$ is H.

The compounds of the invention having structural formula I wherein "a" represents a single bond and "b" represents a double bond may also be prepared, for example by treating a substituted 2-(4-amino-5-pyrazolyl)imidazoline having structural formula VIII

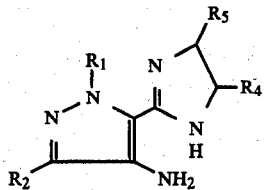

with an orthoester having the formula $R_3C(OR)_3$ wherein $R_1$, $R_2$, $R_3$, $R_4$, and $R_5$ are defined above and R is a convenient alkyl group, preferably ethyl. This reaction may be performed in a nonreactive solvent such as an alcohol, an aromatic hydrocarbon, an ether, and the like. The reaction is best carried out at reflux temperature in the presence of an acid catalyst such as methane sulfonic acid or the acid from which the orthoester is derived. The product is isolated and purified by standard procedures. For example, the reaction mixture is evaporated and the residue is partitioned between dilute base and a solvent such as methylene chloride. The organic layer is separated, dried, evaporated, and the residue is recrystallized.

The starting compound of structural formula VIII may be prepared by the following sequence from a compound having structural formula IX which itself may be prepared by the procedure described in J. Med. Chem., 16, 1346 (1973) or by obvious variations thereof.

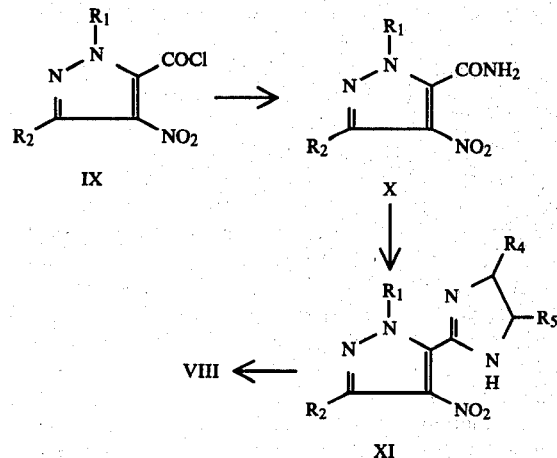

Compound IX may be converted to compound X by, for example treatment with concentrated ammonium hydroxide in a nonreactive solvent such as acetone. Compound X may next be converted to compound XI by treatment with a substituted ethylenediamine having the formula $H_2NCHR_4CHR_5NH_2$. Compound XI may then be reduced, for example with $H_2$/RaNi to produce compound VIII. The reactions in the sequence IX to X to XI to VIII are all within the skill of the art as are any optional variations of the reaction conditions which may be required, for example to improve a particular field. Compound VIII may also be prepared directly from a compound having structural formula XII

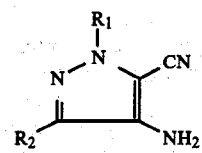

by treatment with an ethylenediamine having the formula $H_2NCHR_4CHR_5NH_2$ by methods familiar to those skilled in the art. Compound XII may be prepared by the method described in U.S. Pat. No. 3,121,092 or by obvious variations thereof.

The compound described above having structural formula IV may be prepared from the corresponding substituted 1,6-dihydro-1H-pyrazolo[4,3-d]pyrimidin-7-one having structural formula XIII

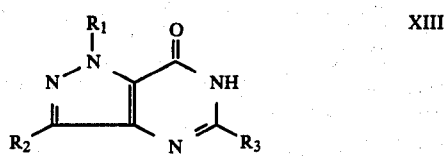

wherein $R_1$, $R_2$, and $R_3$ are defined above. Those skilled in the art will recognize that compound XIII will exist in equilibrium with its tautomeric structure XIII'.

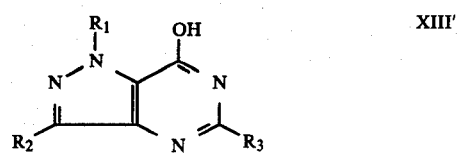

Compound XIII (XIII') may be treated at reflux with a convenient halogenating agent such as a phosphorous pentahalide, a phosphorous trihalide, a thionyl halide, and the like; thereby producing compound IV. Mixtures of the halogenating agents are preferably used and the preferred halogenating agent mixture is phosphorous pentachloride in phosphorous oxychloride. The so produced compound IV is isolated and purified by standard procedures. For example, the reaction mixture is evaporated and the residue is partitioned between chloroform and a dilute aqueous base. The organic solution is separated, dried, evaporated, and the residue purified by crystallized.

Several compounds of formula XIII (XIII') wherein $R_1$ and $R_2$ are methyl are described in U.S. Pat. No. 3,939,161. The procedures described therein as well as obvious variations thereof may be utilized to produce these compounds. Alternatively, XIII (XIII') may be prepared by first converting compound XII to the acyl

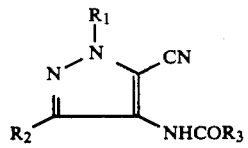

XIV derivative XIV with an acylating reagent, for example an acid halide or an acid anhydride by standard procedures. Compound XIV is then converted to compound XIII (XIII') by treatment with, for example basic aqueous hydrogen peroxide at elevated temperature.

The compound having structural formula XIV may also be prepared from a compound having structural formula X. For example, the amide function of X may be converted to a nitrile by treating X with a dehydrating agent such as phosphorous oxychloride to produce the substituted 5-cyano-4-nitropyrazole. The nitro

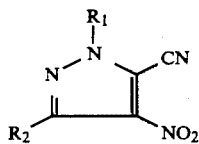

XV substituent of compound XV may be reduced to an amino substituent with, for example iron filings in acetic acid and the so produced correspondingly substituted 5-cyano-4-aminopyrazole may be acylated with, for example an acid anhydride to produce compound XIV.

The compounds of the invention having structural formula I wherein "a" represents a double bond and "b" represents a double bond, compounds Ib, may be prepared by treating a compound having structural formula XVI with an acid such as sulfuric acid. This treatment is

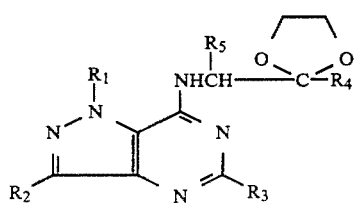

XVI conveniently accomplished with warming without the need for an additional solvent. The compound of structural formula XVI may be prepared from a compound having structural formula IV by treatment with an aminoketal (or acetal) having the formula

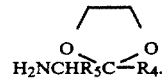

This reaction is carried out substantially as described above for the reaction between compound IV and the substituted ethyleneimine to produce compound V.

Compounds having structural formula Ib may also be prepared by oxidizing a correspondingly substituted compound having structural formula Ia. This oxidation may be conveniently carried out using oxidizing agents such as chloranil, manganese dioxide, and the like under standard conditions.

The compounds of the invention having structural formula I wherein "a" represents a single bond and "b" represents a single bond, compounds Ic, may be prepared, for example, by treating a compound having structural formula VIII with an aldehyde having the formula $R_3CHO$. This reaction is carried out substantially as described above for the reaction between compound VIII and an orthoester to produce a compound having structural formula I wherein "a" represents a single bond and "b" represents a double bond.

The compound of the invention are new chemical substances which are useful as pharmaceutical agents for the treatment of psychoses. The antipsychotic activity of representative compounds of the invention was established by the Mouse Activity and Screen Test Procedure (MAST) described below.

ANIMALS: Nine unfasted Swiss-Webster male mice (Buckberg Labs) weighing 20-30 g are equally divided into three groups for each drug dose to be tested. That is, data for each dose level was generated by three separate groups of three mice each.

DRUGS: A minimum of three dose levels (10, 30, and 100 mg/kg) are tested for each drug. Treatments are administered intraperitoneally one hour prior to testing. All dosages are calculated as parent compound and given in volumes of 10 mg/kg. Compounds are dissolved or suspended in 0.2% Methocel. Control animals are injected with Methocel.

TESTING: A two part testing procedure is started one hour postinjection. First, the screen test is performed (see Pharmac. Biochem. Behav. 6, 351-353, 1977). Briefly this test consists of placing mice on individual wire screens which are then rotated 180 degrees at the start of a 60-second observation period. The number of mice falling off the inverted screen is recorded.

Immediately following the screen test, the final phase of testing is initiated by placing each group of three mice in one actophotometer (Life Sciences, 22, 1067-1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at 10-minute intervals for 60 minutes.

DATA: The data obtained from the screen test are expressed as percent of mice falling off the screen. Data derived from locomotor activity of drug treated mice are compared to the activity of vehicle treated animals and are expressed as percent inhibition of spontaneous locomotion. All percentages reported for inhibition of locomotion are based upon data accumulated for one hour. Both phases of testing are graded: A=60–100%; C=31–59%; and N=0–30%. An overall dose rating is obtained by the following criteria:

| Inhibition of Locomotion Rating | with | Screen Test Failure Rating | = | Dose Rating |
|---|---|---|---|---|
| A | — | N or C | = | A |
| A | — | A | = | C |
| C | — | N or C | = | C |
| | | All other combinations | = | N |

Compounds which exhibit an overall dose rating of A at a dose of 100 milligrams/kilogram or less are considered active. Utilizing this procedure, an overall dose rating of A was obtained for the noted compound at the indicated dose as reported in Table 1.

TABLE 1

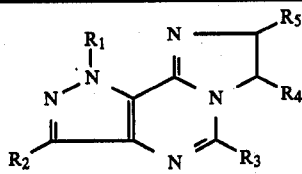

| $R_1$ | $R_2$ | $R_3$ | $R_4$ | $R_5$ | Dose (mg/kg) |
|---|---|---|---|---|---|
| $CH_3$ | $CH_3$ | H | H | H | 100 |
| $CH_3$ | $CH_3$ | H | H | $CH_3$ | 100 |
| $CH_3$ | $CH_3$ | $CH_3$ | H | $CH_3^1$ | 100; 30 |
| $CH_3$ | $CH_3$ | $CH_3$ | H | $CH_3^2$ | 100 |
| $CH_3$ | $CH_3$ | $CH_3$ | H | $CH_3^3$ | 100; 30 |
| $CH_3$ | $CH_3$ | $CH_3$ | $CH_3$ | $CH_3$ | 100 |
| $CH_3$ | $CH_3$ | $CH_3$ | H | $C_2H_5$ | 100; 30 |
| $CH_3$ | $CH_3$ | $CH_3$ | H | $i$-$C_3H_7^2$ | 100 |
| $CH_3$ | $CH_3$ | $CH_3$ | H/$(CH_3)_2^4$ | | 100 |
| $CH_3$ | $CH_3$ | $C_2H_5$ | H | H | $90^5$ |
| $CH_3$ | $CH_3$ | $C_2H_5$ | H | $CH_3$ | 100; 30 |
| $CH_3$ | $CH_3$ | $C_2H_5$ | $CH_3$ | H | 100 |
| $CH_3$ | $CH_3$ | cyc.-$C_3H_5$ | H | $CH_3$ | 100 |
| $C_2H_5$ | $CH_3$ | $CH_3$ | H | H | 100; 30 |
| $C_2H_5$ | $CH_3$ | $CH_3$ | H | $CH_3$ | 100; 30 |
| $C_2H_5$ | $CH_3$ | $C_2H_5$ | H | $CH_3$ | 100 |
| n-$C_3H_7$ | $CH_3$ | $CH_3$ | H | $CH_3$ | 100 |
| $CF_3CH_2$ | $CH_3$ | $CH_3$ | H | $CH_3$ | 100 |

[1]Racemate
[2]S-isomer
[3]R-isomer
[4]Indicates that one of $R_4$ or $R_5$ and the other substituent is $(CH_3)_2$.
[5]Compound administered orally In order to further assess their usefulness, representative compounds of the invention were tested in a conditioned avoidance-escape procedure. In this test*, an animal (male Wistar rat) is conditioned to respond to a stimulus in order to avoid an unpleasant electrical shock. Should the animals fail to give the response in order to avoid the shock, an escape route is available so that it can escape the shock once it is delivered. Preferably, compounds will show variations between the dose that will supress conditioned avoidance and the dose that will suppress the escape response.

*Modification of the pole-climb avoidance paradigm described in Ann. NY Acad. Sci., 740, (1957).

The results obtained for representative compounds of the invention in such a procedure are displayed in Table 2.

TABLE 2

| | | | | | Oral ED50 mg/kg | |
|---|---|---|---|---|---|---|
| $R_1$ | $R_2$ | $R_3$ | $R_4$ | $R_5$ | Avoidance | Escape |
| $CH_3$ | $CH_3$ | H | H | H | 18 | 54 |
| $CH_3$ | $CH_3$ | H | H | $CH_3$ | 18 | 56 |
| $CH_3$ | $CH_3$ | $CH_3$ | H | $CH_3^1$ | 10 | 32 |
| $CH_3$ | $CH_3$ | $CH_3$ | H | $CH_3^2$ | 11.5 | 20 |
| $CH_3$ | $CH_3$ | $CH_3$ | H | $CH_3^3$ | <65 | <65 |
| $CH_3$ | $CH_3$ | $CH_3$ | $CH_3$ | $CH_3$ | 20 | 57 |
| $CH_3$ | $CH_3$ | $CH_3$ | H | $C_2H_5$ | 7.5 | 32 |
| $CH_3$ | $CH_3$ | $CH_3$ | H | $i$-$C_3H_7^2$ | 20 | 70 |
| $CH_3$ | $CH_3$ | $CH_3$ | $(CH_3)_2$ | $H_2$ | 32 | 80 |
| $CH_3$ | $CH_3$ | $CH_3$ | $H_2$ | $(CH_3)_2$ | 18 | 120 |
| $CH_3$ | $CH_3$ | $C_2H_5$ | H | $CH_3$ | 6.4 | 66 |
| $CH_3$ | $CH_3$ | $C_2H_5$ | $CH_3$ | H | 35 | 52 |
| $CH_3$ | $CH_3$ | cyc.-$C_3H_5$ | H | $CH_3$ | 11.5 | 110 |
| $C_2H_5$ | $CH_3$ | $CH_3$ | H | H | 10 | 28 |
| $C_2H_5$ | $CH_3$ | $CH_3$ | H | $CH_3$ | 5 | 15 |
| $C_2H_5$ | $CH_3$ | $C_2H_5$ | H | $CH_3$ | 9 | 50 |
| n-$C_3H_7$ | $CH_3$ | $CH_3$ | H | $CH_3$ | 37 | 90 |
| $CH_3$ | $CH_3$ | $C_2H_5$ | H | $CH_3^4$ | 8 | 45 |

[1]Racemate
[2]S-isomer
[3]R-isomer
[4]Double bond at a.

The compounds of the invention form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, and the like. The salts are prepared by contacting the free base form with a sufficient amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups contemplated by the invention comprise both straight and branched carbon chains of from one to about six carbon atoms. Representative of such groups are methyl, ethyl, isopropyl, pentyl, 3-methylpentyl, and the like.

The term fluorinated alkyl is intended to include trifluoromethyl, $\beta,\beta,\beta$-trifluoroethyl and the like.

The term inorganic halogenating agent when utilized herein includes for example $POCl_3$, $PCl_3$, $PCl_5$, $SOCl_2$, $PBr_3POBr_3$, and the like as well as mixtures thereof. Similar equivalent agents will be familiar to those skilled in the art.

Some of the compounds of the invention may comprise an asymmetric carbon atom. The pure D isomer, pure L isomer, as well as mixtures thereof are contemplated by the invention. Asymmetric carbon atoms may be present in a substituent such as an alkyl group. All such isomers as well as mixtures thereof are intended to be included in the invention.

The compounds of the invention can be prepared and administered in a wide variety of oral and parenteral dosage forms. It will be obvious to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as antipsychotic agents, the compounds utilized in the pharmaceutical method of this invention are administered at the initial dosage of about 0.1 mg to about 100 mg per kilogram daily. A daily dose range of about 1.0 mg to about 50 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

7,8-Dihydro-1,3-dimethyl-1H-imidazo[1,2-c]pyrazolo[3,4-e]pyrimidine 1,3-Dimethyl-4-nitro-5-pyrazolecarboxamide (28 g, 0.15 mol) is added to a solution of 38 g (0.2 mol) of triethyloxonium fluoroborate in 250 ml of methylenedichloride. The mixture is stirred at 20° C. for six hours and evaporated in vacuo. The residue is dissolved in 200 ml of absolute ethanol and 18 g (0.3 mol) of ethylenediamine is added. The yellow solution is stirred overnight at 20° C. and the solvent is evaporated in vacuo. The residue is stirred in 300 ml of 2N hydrochloric acid and filtered from 11.5 g (41%) of recovered starting amide. The filtrate is made basic with sodium carbonate and extracted with methylenedichloride. Evaporation of the methylenedichloride gives 9 g of 2-(1,3-dimethyl-4-nitro-5-pyrazolyl)imidazoline, mp 143°–145° C. from ethyl acetate-pet ether.

The above nitro compound (8.4 g, 0.04 mol) is dissolved in 150 ml of methanol and hydrogenated (initial hydrogen pressure=51 psi) in the presence of 0.5 g of Raney nickel until the theoretical uptake of hydrogen is observed. The catalyst is removed by filtering; the filtrate is evaporated in vacuo to give 7.4 g (0.04 mol) of a purple oil (characterized by its IR-spectrum) of 2-(4-amino-1,3-dimethyl-5-pyrazolyl)imidazoline. This amine (7.4 g, 0.04 mol) is stirred under reflux 1.5 hr in a mixture of 20 ml absolute ethanol, 50 ml of triethylorthoformate and 1 ml of methanesulfonic acid. The mixture is evaporated in vacuo. The product is dissolved in methylenedichloride (100 ml) and washed with 100 ml of dilute ammonium hydroxide; the organic layer is dried over MgSO$_4$ and evaporated in vacuo to give 7,8-dihydro-1,3-dimethyl-1H-imdazo[1,2-c]pyrazolo[3,4-e]pyrimidine 1.5 hydrate, mp 80°–82° C. from ethyl acetate-pet ether.

EXAMPLE 2

7,8-Dihydro-1,3,8-trimethyl-1H-imidazo[1,2-c]pyrazolo[3,4-e]pyrimidine 7,8-Dihydro-1,3-dimethyl-1H-pyrazolo[4,3-d]-pyrimidine-7-one (8 g, 0.05 mol) is added to a stirred suspension of 11 g (0.05 mol) phosphorus pentachloride in 200 ml of phosphorus oxychloride and the mixture is stirred under reflux for 3.5 hr and evaporated in vacuo. The residue is dissolved in chloroform (150 ml) and stirred with 150 ml of saturated aqueous sodium bicarbonate. The organic layer is separated, dried over $MgSO_4$ and evaporated in vacuo to give 9 g of 7-chloro-1,3-dimethyl-1H-pyrazolo[4,3-d]pyrimidine, mp 92°–95° C. from pet ether.

The above chloropyrimidine (9 g, 0.05 mol) is dissolved in 100 ml of methylene dichloride and treated with 8 ml of triethylamine and 6 g (0.1 mol) of 2-methylaziridine. After standing at room temperature overnight, the reaction mixture is washed with saturated aqueous sodium bicarbonate solution, dried over $MgSO_4$ and evaporated in vacuo to give 9 g of 1,3-dimethyl-7-(2-methylaziridinyl)-1H-pyrazolo[4,3-d]pyrimidine as an oil, characterized by its NMR-spectra.

The above aziridine (9 g, 0.044 mol) is dissolved in 100 ml of acetone, sodium iodide (8 g, 0.053 mol) is added and the mixture is refluxed 1.5 hr and evaporated in vacuo. The residue is partitioned in 150 ml of methylene dichloride and 60 ml of 20% sodium carbonate solution. The organic layer is separated, dried ($MgSO_4$) and evaporated in vacuo to give 8 g (89%) of 7,8-dihydro-1,3,8-trimethyl-1H-imidazo[1,2-c]pyrazolo[3,4-e]pyrimidine, mp 115°–117° C. from heptane.

7,8-Dihydro-1,3-dimethyl-1H-pyrazolo[4,3-d]pyrimidin-7-one

Twenty-four ml of 30% hydrogen peroxide is added dropwise to a solution of 6 g (0.15 mol) sodium hydroxide in 200 ml of water at 40° C. N-(5-cyano-1,3-dimethylpyrazol-4-yl)formamide (14.5 g, 0.088 mol) is added in portions, and the mixture is stirred at 80° C. for four hours. The solution is acidified with glacial acetic acid and the precipitate is collected by filtering to give 8 g (56%) of title compound, mp 298°–300° C.

The starting material is obtained by treating 16 g (0.12 mol) of 4-amino-5-cyano-1,3-dimethyl pyrazole [U.S. Pat. No. 3,121,092: CA 60 2030 (1964)] with acetic-formic anhydride (prepared by adding 45 ml of acetic anhydride to 20 ml of 98% formic acid at 50° C.). After standing at room temperature overnight, the solution is evaporated in vacuo. The residue is stirred in ether to give 14.5 g (74%) of N-(5-cyano-1,3-dimethylpyrazol-4-yl) formamide, mp 135° C.

EXAMPLE 3

7,8-Dihydro-1,3,5,8-tetramethyl-1H-imidazo[1,2-c]pyrazolo[3,4-]pyrimidine

A mixture of 30.5 g (0.17 mol) of 1,3,5-trimethyl-1H-pyrazolo[4,3-d]pyrimidin-7-ol and 37 g (0.18 mol) of phosphorus pentachloride in 350 ml of phosphorus oxychloride is stirred under reflux for seven hours and the resulting solution is evaporated in vacuo. The solid residue is redissolved in 300 ml of methylenedichloride and stirred with 200 ml of a saturated aqueous solution of sodium bicarbonate. The organic layer is dried over $MgSO_4$ and evaporated in vacuo to give 30 g (98%) of 7-chloro-1,3,5-trimethyl-1H-pyrazolo[4,3-d]pyrimidine, mp 91°–93° C. from ethyl acetate-pet ether.

The above chloro compound (30 g, 0.153 mol) is dissolved in 300 ml of methylenedichloride, cooled in an ice bath, and treated dropwise with 28 ml (0.2 mol) of triethylamine and 17 g (0.3 mol) of 2-methylaziridine. After standing at 20° C. for two days, the solution is washed with a sodium bicarbonate solution, dried over $MgSO_4$ and evaporated in vacuo to give 34 g of 7-(2-methylaziridinyl)-1,3,5-trimethylpyrazolo[4,3-d]pyrimidine as an oil characterized by IR, NMR, TLC, and elemental analyses.

The above aziridine (4.4 g, 0.02 mol) in 50 ml of acetone is stirred under reflux with 3.5 g of sodium iodide for three hours and evaporated in vacuo. The residue is partitioned in 150 ml of methylene dichloride and 50 ml of 20% aqueous sodium carbonate solution. The organic layer is separated, dried ($MgSO_4$) and evaporated in vacuo. The resulting solid is recrystallized from acetonitrile to give 2.5 g of the title compound, mp 169°–172° C.

Preparation of 1,3,5-trimethyl-1H-pyrazolo[4,3-d]pyrimidin-7-ol

A solution of 102 g (0.5 mol) of 1,3-dimethyl-4-nitropyrazolo-5-carbonyl chloride [J. Med. Chem. 16 1347 (1973)] in 100 ml of acetone is added dropwise to 450 ml of cold concentrated ammonium hydroxide with stirring. Stirring was continued one hour, then the mixture was filtered to give 85 g (92%) of 1,3-dimethyl-4-nitropyrazole-5-carboxamide mp 153°–155° C.

This amide (42 g, 0.23 mol) in 300 ml of 95% ethanol and 50 ml of water is treated with 50 g of iron powder (reduced) and 4 ml of concentrated HCl and the mixture is stirred under reflux 3.5 hours. The mixture is filtered and the filtrate is evaporated to dryness. The 4-amino-1,3-dimethylpyrazole-5-carboxamide melts at 153°–155° from ethyl acetate. This product is suspended in 300 ml methylene dichloride, and 30 ml of acetic anhydride is added dropwise with stirring. After stirring overnight, the mixture is diluted with 100 ml of pet ether and filtered to give 38 g (85%) of N-(5-carboxamido-1,3-dimethylpyrazol-4-yl)acetamide, mp 247°–249° C. The product (38 g, 0.19 mol) is stirred in 365 ml of 1N sodium hydroxide at 80°–90° C. for three hours, cooled and acidified with 30 ml of glacial acetic acid to give 28.5 g (75%) of 1,3,5-trimethyl-1H-pyrazolo[4,3-d]pyrimidin-7-ol, mp 258°–260° C.

EXAMPLE 4

7,8-Dihydro-1,3,5,8-tetramethyl-1H-imidazo[1,2-c]pyrazolo[3,4-e]pyrimidine (S-form)

A mixture of 7-chloro-1,3,5-trimethyl-1H-pyrazolo[4,3-d]pyrimidine (Ex. 3) (7 g, 0.036 mol) and 4 g (0.053 mol) of L-2-amino-1-propanol (L-alaninol) and 6 ml of triethylamine is heated in 75 ml of toluene on the steam bath for four hours and refrigerated. The mixture is filtered to give a hygroscopic solid which is stirred in 20 ml of 6N ammonium hydroxide. Filtration gives 4.5 g (53%) of S-2-[1,3,5-trimethyl-1H-pyrazolo[4,3-d]pyrimidin-7-yl]amino-1-propanol, mp 197°–199° C.

The above compound (4.5 g, 0.02 mol) is refluxed 1.5 hr in 50 ml of phosphorus oxychloride and the solution is evaporated in vacuo. The residue is dissolved in methylene dichloride (100 ml) and stirred with excess 3N ammonium hydroxide. The organic portion is separated, dried over anhydrous $MgSO_4$, and evaporated in vacuo to give 3.9 g (90%) of title compound, mp 173°–175° C. from acetonitrile; $[\alpha]_D^{23} -124°$ C., c 1.13% in methanol.

EXAMPLE 5

7,8-Dihydro-1,3,5-trimethyl-1H-imidazo[1,2-c]-pyrazolo[3,4-e]pyrimidine (R-form)

D-alanine methyl ester hydrochloride (6 g, 0.043 mol) is dissolved in 30 ml of cold (5° C.) dimethylformamide and 7 ml (0.05 mol) of triethylamine is added dropwise. After stirring 15 minutes, 6 g of triethylamine hydrochloride is removed by filtering. To the filtrate is added 7 g (0.035 mol) of 7-chloro-1,3,5-trimethyl-1H-pyrazolo-[4,3-d]pyrimidine and another 6 ml of triethylamine. The mixture is stirred at 50°-55° C. for 60 hours and evaporated in vacuo. The residue is dissolved in 100 ml of methylene dichloride, washed with saturated sodium bicarbonate solution, dried over magnesium sulfate and evaporated in vacuo to give 7.6 g of slightly impure (R)-2-[1,3,5-trimethyl-1H-pyrazolo[4,3-d]pyrimidin-7-yl]aminopropionic acid, methyl ester, mp 68°-70° C. from ether as a dihydrate.

The above ester (7.6 g, 0.029 mol) is dissolved in 100 ml of 95% ethanol. Sodium borohydride (0.06 mol) is added and the mixture is stirred under reflux three hours. Sodium hydroxide (30 ml, 1N) is added and refluxing continued for 0.5 hours to hydrolyze borate esters. The mixture is concentrated in vacuo to about 30 ml volume and filtered to give 4.6 g (67%) of R-2-[1,3,5-trimethyl-1H-pyrazolo[4,3-d]pyrimidin-7-yl]amino-1-propanol, mp 199°-201°.

The above amino alcohol (4.2 g, 0.018 mol) is refluxed in 50 ml of phosphorus oxychloride for 1.5 hours and the solution is evaporated in vacuo. The residue is dissolved in methylene dichloride (100 ml) and stirred with 100 ml of 4N ammonium hydroxide. The organic layer is separated, dried over magnesium sulfate and evaporated in vacuo to give 2.8 g (72%) of the title compound, mp 174°-177° C.

$[\alpha]_D^{23} + 105°$, c 1.06 in methanol.

EXAMPLE 6

7,8-Dihydro-1,3,5,7,8-pentamethyl-1H-imidazo[1,2-c]pyrazolo[3,4-e]pyrimidine A mixture of 7 g (0.05 mol) of 4-amino-5-cyano-1,3-dimethylpyrazole, 5 g (0.057 mol) of 2,3-diaminobutane and 10.5 g (0.055 mol) of p-toluene sulfonic acid hydrate is heated in an oil bath at 180°-200° C. for seven hours. The yellow melt is dissolved in 200 ml of chloroform and stirred with 100 ml of 20% aqueous sodium carbonate solution. The organic layer is separated, dried over MgSO4 and evaporated in vacuo to give 9.5 g of 2-(4-amino-1,3-dimethyl-5-pyrazolyl)-4,5-dimethylimidazoline and characterized as a dihydrochloride salt, mp 250° C. from 20% isopropanolic HCl and ethyl acetate.

A mixture of 9 g (0.045 mol) of the above imidazoline, 16 g (0.1 mol) of triethylorthoacetate, and 5 ml of acetic acid in 150 ml of toluene is stirred under reflux overnight. The partly cooled mixture is extracted with 150 ml of 1N hydrochloric acid. After standing one hour, the aqueous solution is made basic with concentrated ammonium hydroxide and extracted with chloroform. The chloroform extract is dried over MgSO4 and evaporated in vacuo. The residual oil (9 g) is chromatographed over silica gel in acetonitrile and eluted with methanol to give 6.4 g of oil. The oil is dissolved in 35 ml of ethyl acetate, treated with 20 ml of 20% isopropanolic HCl and diluted with ether to give 3.5 g (25%) of the title compound as the dihydrochloride salt, mp 280° C.

EXAMPLE 7

8-Ethyl-7,8-dihydro-1,3,5-trimethyl-1H-imidazo[1,2-c]pyrazolo[3,4-e] pyrimidine A mixture of 8 g (0.04 mol) of 7-chloro-1,3,5-trimethyl-1H-pyrazolo[4,3-d]pyrimidine (Ex. 3) and 9 g (0.1 mol) of 2-amino-1-butanol in 75 ml of toluene is heated on the steam bath four hours. The warm solution is shaken with 100 ml of 4N ammonium hydroxide. The aqueous extract is concentrated in vacuo to give 3 g of 2-[1,3,5-trimethyl-1-H-pyrazolo[4,3-d]pyrimidin-7-yl]amino-1-butanol, mp 165°-168° C. Another 2.2 g of product is obtained by concentrating the toluene solution.

This amino alcohol (5 g, 0.02 mol) is refluxed 1.5 hours in 75 ml of phosphorus oxychloride and the solution is evaporated in vacuo. The residue is dissolved in 100 ml of methylene dichloride and stirred with excess 6N ammonium hydroxide; the organic layer is separated, dried over magnesium sulfate, and evaporated in vacuo to give 4 g (85%) of the title compound, mp 121°-123° C. from acetonitrile.

EXAMPLE 8

7,8-Dihydro-8-isopropyl-1,3,5-trimethyl-1H-imidazo[1,2-c]pyrazolo[3,4-e]pyrimidine dihydrochloride (S-form)

A mixture of 8 g (0.04 mol) of 7-chloro-1,3,5-trimethyl-1H-pyrazolo[4,3-d]pyrimidine (Ex. 3), 4.5 g (0.045 mol) of L-valinol (2-amino-3-methyl-1-butanol) and 8 ml of triethylamine in 50 ml of dimethylformamide is stirred at 50°-55° C. for 50 hours and evaporated in vacuo. The residue is dissolved in methylene dichloride, washed with a saturated solution of sodium bicarbonate, dried over MgSO4, and evaporated in vacuo. The residue is stirred in pet ether to give 4.8 g (45%) of 2-[1,3,5-trimethyl-1H-pyrazolo[4,3-d]-pyrimidine-7-yl]amino-3-methyl-1-butanol, mp 166°-168° C. from acetonitrile.

The above aminoalcohol (6.5 g, 0.0247 mol) is refluxed in 75 ml of phosphorus oxychloride for 1.5 hours. The red solution is evaporated in vacuo. The residue is dissolved in methylene dichloride and stirred with excess 3N ammonium hydroxide. The organic layer is separated, dried over MgSO4, and evaporated in vacuo. The residue is dissolved in 20 ml of 20% isopropanolic HCl and diluted with ethyl acetate and ether to turbidity. The resulting precipitate is collected to give 2.9 g (37%) of the title compound as the dihydrochloride salt, mp 185°-187° C.

EXAMPLE 9

7,8-Dihydro-1,3,5,7,7-pentamethyl-1H-imidazo[1,2-c]pyrazolo[3,4-e]pyrimidine A mixture of 9 g (0.044 mol) of 2-(4-amino-1,3-dimethyl-5-pyrazolyl)-3,3-dimethylimidazoline, 16 g (0.1 mol) of triethylorthoacetate and 5 ml of acetic acid in 150 ml of toluene is stirred under reflux 16 hours. The warm solution is extracted with 150 ml of 1N hydrochloric acid. The aqueous extract is made basic with conc. ammonium hydroxide and extracted with methylene dichloride. The extract is dried and evaporated in vacuo. The residue is percolated over silica gel in acetonitrile-methanol to give 7 g of crude product. A sample of the free base is crystallized from acetonitrile with a melting range of 128°-135° C. The remainder is dissolved in 30 ml of 20% isopropanolic HCl and diluted with ethyl acetate and ether to give 3.85 g (29%)

of the title compound, as the dihydrochloride salt, mp 280°-283° C.

The requisite 2-(4-amino-1,3-dimethyl-5-pyrazolyl)-3,3-dimethylimidazoline is prepared as follows. p-Toluenesulfonic acid (10 g, 0.055 mol) is added to 5 g (0.057 mol) of 1,2-diamino-2-methylpropane and to the resulting hot (100°) melt is added 7 g (0.05 mol) of 4-amino-5-cyano-1,3-dimethylpyrazole. The mixture is heated in an oil bath at 185°-195° C. for six hours. The residue, an amorphous yellow solid is dissolved in 250 ml of chloroform and stirred with 40 ml of conc. ammonium hydroxide. The organic layer is separated, dried (MgSO$_4$), and evaporated in vacuo to give 9 g (90%) of slightly crude title compound as a viscous purple oil.

EXAMPLE 10

7,8-Dihydro-1,3,5,8,8-pentamethyl-1H-imidazo[1,2-c]pyrazolo[3,4-e]pyrimidine

A mixture of 9.5 g (0.05 mol) of 7-chloro-1,3,5-trimethyl-1H-pyrazolo[4,3-d]pyrimidine (Example 3), 6.5 g (0.073 mol) of 2-amino-2-methyl-1-propanol and 8 ml of triethylamine in 30 ml of dimethylformamide is stirred at 50°-55° C. for 20 hours and evaporated in vacuo. The residue is dissolved in 150 ml of methylene dichloride and washed with 75 ml of conc. ammonium hydroxide. The organic solution is dried over MgSO$_4$ and evaporated in vacuo. The residue is crystallized from ether-pet ether to give 7 g (53%) of 2-[1,3,5-trimethyl-1H-pyrazolo[4,3-d]pyrimidin-7-yl]-2-amino-2-methyl-1-propanol, mp 185°-187° from ethyl acetate.

A solution of 5.3 g (0.02 mol) of this aminoalcohol in 400 ml of methylene dichloride is treated with 6 g (0.04 mol) of phosphorus oxychloride and stirred under reflux for three hours. The cooled reaction mixture is stirred with 100 ml of 3N ammonium hydroxide, the organic layer is separated, dried over MgSO$_4$, and evaporated in vacuo to give 4 g (86%) of the title compound, mp 148°-150° C. from toluene-pet ether.

EXAMPLE 11

5-Ethyl-7,8-dihydro-1,3-dimethyl-1H-imidazo[1,2-c]pyrazolo[3,4-e]pyrimidine

A mixture of 27 g (0.14 mol) of 5-ethyl-1,3-dimethyl-1H-pyrazolo[4,3-d]pyrimidin-7-ol and 30 g (0.15 mol) of phosphorus pentachloride in 300 ml of phosphorus oxychloride is stirred under reflux for two hours and evaporated in vacuo. The residue is dissolved in 300 ml of methlene dichloride and stirred with 300 ml of a saturated aqueous solution of sodium bicarbonate. The organic layer is dried over anhydrous MgSO$_4$ and evaporated in vacuo to yield 21 g (71%) of 7-chloro-5-ethyl-1,3-dimethylpyrazolo[4,3d]pyrimidine as an oil.

This chloropyrimidine (6 g, 0.03 mol) is dissolved in 75 ml of methylene dichloride and treated at 5° C. with 10 ml of ethyleneimine. After standing overnight at room temperature, the mixture is washed with a saturated aqueous solution of NaHCO$_3$, dried over MgSO$_4$, and evaporated in vacuo to yield 6 g of 7-(1-aziridinyl)-1,3-dimethyl-5-ethyl-1H-pyrazolo[4,3-d]pyrimidine as an oil.

The above aziridine (6 g, 0.03 mol) is dissolved in 100 ml of acetone and refluxed with 6 g of sodium iodide for two hours. The solution is evaporated in vacuo. The residue is dissolved in methylene dichloride, washed with saturated NaHCO$_3$ solution, dried over MgSO$_4$, and evaporated in vacuo. The resulting solid (2.3 g, 38% yield) melts at 148°-150° C. after recrystallization from ethyl acetate.

Preparation of 5-ethyl-1,3-dimethyl-1H-pyrazolo[4,3-d]pyrimidin-7-ol

A mixture of 14 g (0.1 mol) of 4-amino-5-cyano-1,3-dimethylpyrazole and 14 g (0.11 mol) of propionic anhydride in 120 ml of ethyl acetate is stirred under reflux 3.5 hours and evaporated in vacuo. The residue is treated with ether and filtered to give 18 g (94%) of N-(5-cyano-1,3-dimethyl-1H-pyrazol-4-yl)propionamide, mp 153°-155° C. from ethanol.

The above propionamide (18 g, 0.094 mol) is added in portions to a solution prepared by adding 24 ml of 30% hydrogen peroxide to 250 ml of water containing 6 g (0.15 mol) of sodium hydroxide. The mixture is stirred at 80° C. for five hours, cooled and acidified with acetic acid to give 12.7 g (70%) of 5-ethyl-1,3-dimethyl-1H-pyrazolo[4,3-d]pyrimidin-7-ol, mp 220°-222° C. from ethanol.

EXAMPLE 12

7,8-Dihydro-5-ethyl-1,3,8-trimethyl-1H-imidazo[1,2-c]pyrazolo[3,4-e]pyrimidine

A mixture of 10 g (0.047 mol) of 7-chloro-5-ethyl-1,3-dimethyl-pyrazolo[4,3-d]pyrimidine (Ex. 11), 10 ml of triethylamine and 12 ml (0.17 mol) of 2-methylaziridine in 200 ml of methylenedichloride is allowed to stand overnight at room temperature. The reaction mixture is washed with saturated sodium bicarbonate solution; the organic layer is dried over magnesium sulfate, and evaporated in vacuo to give 10 g of product as an oil. The oil (10 g) is dissolved in 150 ml of acetone and refluxed three hours with 10 g of sodium iodide. The mixture is evaporated in vacuo. The residue is dissolved in 100 ml of methylene dichloride, washed with sodium bicarbonate solution, dried, and evaporated. Crystallization of the residue from ethyl acetate gives 3.3 g (33%) of the title compound, mp 153°-155° C.

EXAMPLE 13

7,8-Dihydro-5-ethyl-1,3,7-trimethyl-1H-imidazo[1,2-c]pyrazolo[3,4-e]pyrimidine

A mixture of 10.5 g (0.05 mol) of 7-chloro-5-ethyl 1,3-dimethylpyrazolo[4,3-d]pyrimidine (Ex. 11) 7.5 g (0.1 mol) of 1-amino-2-propanol and 8 ml of triethylamine in 75 ml of methylene dichloride is stirred at room temperature for 60 hours and filtered. The hygroscopic solid is stirred in 50 ml of saturated sodium bicarbonate solution to give 9.5 g (76%) of 1-[1,3-dimethyl-5-ethyl-1H-pyrazolo[4,3-d]pyrimidin-7-yl]amino-2-propanol, a hemihydrate melting at 116°-119° C. from ethyl acetate-pet ether.

The above compound 7.2 g (0.03 mol) is refluxed in 80 ml of phosphorus oxychloride for 1.5 hours and the mixture is evaporated in vacuo. The residual oil is dissolved in 100 ml of methylene dichloride and stirred with excess 2N ammonium hydroxide. The organic portion is separated, dried over anhydrous magnesium sulfate and evaporated in vacuo. The residue is crystallized from pet ether to give 4.5 g (65%) of the title compound, mp 105°-107° C.

EXAMPLE 14

5-Cyclopropyl-7,8-dihydro-1,3,8-trimethyl-1H-imidazo[1,2-c]pyrazolo[3,4-e]pyrimidine A mixture of 5-cyclopropyl-1,3-dimethyl-1H-pyrazolo[4,3-d]pyrimidin-7-ol (14.3 g, 0.07 mol) and 18 g (0.088 mol) phosphorus pentachloride in 150 ml of phosphorus oxychloride is stirred under reflux for seven hours and evaporated in vacuo. The residue is dissolved in methylene dichloride and stirred with a saturated aqueous solution of NaHCO$_3$. The organic layer is separated, dried (MgSO$_4$), and evaporated in vacuo to give 13.9 g (84%) of 7-chloro-5-cyclopropyl-1,3-dimethyl-pyrazolo[4,3-d]pyrimidine, mp 87°–90° C. from heptane.

The above chloro compound (12.7 g, 0.056 mol) is dissolved in 200 ml of methylene dichloride and treated with 12 ml of triethylamine and 13.5 ml of 2-methylaziridine. After standing at room temperature for two days, the mixture is washed with saturated NaHCO$_3$ solution, dried (MgSO$_4$), and evaporated in vacuo to give 12.2 g (84%) of 5-cyclopropyl-1,3-dimethyl-4-[(2-methyl)-1-aziridinyl]pyrazolo[4,3-d]pyrimidine, characterized by IR and NMR-spectra.

The above aziridine (12 g, 0.05 mol) is dissolved in 100 ml of acetone and refluxed with 10 g of sodium iodide for 2.5 hours. The mixture is evaporated in vacuo. The residue is dissolved in methylene dichloride and washed with a saturated solution of NaHCO$_3$. The organic solution is dried (MgSO$_4$) and evaporated in vacuo. The residual oil is crystallized from ethyl acetate ether to give 3.1 g (30%) of title compound, mp 107°–110° C.

Preparation of 5-cyclopropyl-1,3-dimethyl-1H-pyrazolo[4,3-d]pyrimidin-7-ol

4-Amino-5-cyano-1,3-dimethylpyrazole [U.S. Pat. No. 3,121,092 C.A. 60 2030 (1964)] (13.6 g, 0.1 mol) is mixed with 15 ml of triethylamine in 150 ml of methylene dichloride, cooled to 10° C., and treated dropwise with 11 g (0.107 mol) of cyclopropane carbonyl chloride. After stirring overnight at room temperature, a saturated solution of NaHCO$_3$ solution is added. The mixture is filtered to give 14.3 g (71%) of N(5-cyano-1,3-dimethylpyrazol-4-yl)cyclopropylcarboxamide carboxamide.

The above amide (12.5 g, 0.061 mol) is added in portions to a stirred solution of 22 ml of 30% hydrogen peroxide and 200 ml of water containing 5 g of sodium hydroxide. The mixture is stirred overnight at 80°–90° C., then acidified with glacial acetic acid, cooled and filtered to give 6.3 g (50%) of 5-cyclopropyl-1,3-dimethyl-1H-pyrazolo[4,3-d]pyrimidin-7-ol, mp 238°–240° C.

EXAMPLE 15

7,8-Dihydro-5-isopropyl-1,3,8-trimethyl-1H-imidazo[1,2-c]pyrazolo[3,4-e]pyrimidine A mixture of 10 g (0.048 mol) of 1,3-dimethyl-5-isopropyl-1H-pyrazolo[4,3-d]pyrimidin-7-ol and 10.2 g (0.049 mol) of phosphorus pentachloride in 70 ml of phosphorus oxychloride is stirred under reflux five hours and evaporated in vacuo. The residue is dissolved in 150 ml of methylene dichloride and stirred with 100 ml of a saturated solution of sodium bicarbonate. The organic layer is separated, dried over MgSO$_4$, and evaporated in vacuo to to give 10.5 g of 7-chloro-1,3-dimethyl-5-isopropyl-1H-pyrazolo[4,3-d]pyrimidine, mp 87°–89° C. from pet ether.

A solution of the above chloro pyrimidine (10 g, 0.045 mol), 10 ml of 2-methylaziridine and 9 ml of triethylamine is allowed to stand at room temperature overnight. The reaction mixture is washed with saturated sodium bicarbonate and evaporated in vacuo. The oil (11 g) is percolated over silica gel in ethyl acetate to give 7 g (64%) of 1,3-dimethyl-5-isopropyl-7-(2-methylaziridinyl)-1H-pyrazolo[4,3-d]pyrimidine as an oil.

The aziridine (6.7 g, 0.027 mol) in 100 ml of acetone is refluxed two hours with 4.5 g (0.03 mol) of sodium iodide and the mixture is evaporated in vacuo. The residue is partitioned in 100 ml of methylene dichloride and 50 ml of saturated sodium bicarbonate solution. The organic layer is separated, dried over magnesium sulfate, and evaporated in vacuo. The oil is crystallized from pet ether to give 3.6 g (54%) mp 96°–97° C. of 7,8-dihydro-5-isopropyl-1,3,8-trimethyl-1H-imidazo[1,2-c]pyrazolo[3,4-e]pyrimidine.

Preparation of 1,3-dimethyl-5-isopropyl-1H-pyrazolo[4,3-d]pyrimidin-7-ol

A solution of 24 g (0.176 mol) of 4-amino-5-cyano-1,3-dimethylpyrazole and 28 ml of triethylamine in 200 ml of chloroform is treated dropwise with 19.3 g (0.18 mol) of isobutyryl chloride and stirred overnight. The mixture is stirred with 100 ml of saturated sodium bicarbonate solution, the organic layer is separated and evaporated in vacuo. The residue is crystallized from ethyl acetate to give 30 g (83%) of N-(5-cyano-1,3-dimethyl-pyrazol-4-yl)isobutyramide. This amide (30 g, 0.0146, mol) is added in portions to a solution of 7.1 g (0.017 mol) sodium hydroxide in 250 ml of water containing 36 ml of 30% hydrogen peroxide at 80° C. After stirring at 80° C. overnight, the solution is cooled and acidified with glacial acetic acid to give 23 g (74%) of 1,3-dimethyl-5-isopropyl-1H-pyrazolo[4,3-d]pyrimidin-7-ol, mp 264°–266° C.

EXAMPLE 16-a

1-Ethyl-7,8-dihydro-3,5-dimethyl-1H-imidazo[1,2-c]pyrazolo[3,4-e]pyrimidine

A mixture of 16 g (0.083 mol) of 3,5-dimethyl-1-ethyl-7-hydroxy-1H-pyrazolo[4,3-d]pyrimidine and 18.5 g (0.087 mol) of phosphorus pentachloride in 120 ml of phosphorus oxychloride is stirred under reflux five hours. The solution is evaporated in vacuo. The residue is redissolved in ether and percolated over neutral alumina to yield 15 g of 7-chloro-3,5-dimethyl-1-ethyl-1H-pyrazolo[4,3-d]pyrimidine, a low-melting waxy solid (40°–50° C.).

This chloropyrazolopyrimidine (15 g, 0.07 mol) is dissolved in methylene dichloride (100 ml) and a solution of 20 ml of ethyleneimine in 30 ml of CH$_2$Cl$_2$ is added dropwise at 0° C. After standing overnight at room temperature, the solution is stirred with 100 ml of saturated aqueous solution of NaHCO$_3$. The organic layer is separated, dried over MgSO$_4$, and evaporated in vacuo to give 14 g of 7-(1-aziridinyl)-3,5-dimethyl-1-ethyl-1H-pyrazolo[4,3-d]pyrimidine, mp 66°–69° C. from pet ether.

The above aziridine (14 g, 0.065 mol) is dissolved in 150 ml acetone and 12 g (0.08 mol) of sodium iodide is added. The mixture is stirred overnight as a solid separates. The cooled mixture is filtered, the filter cake is washed with saturated NaHCO₃ solution then water to yield 8 g (57%) of the title compound, mp 168°–170° C.

Preparation of
1-ethyl-3,5-dimethyl-1H-pyrazolo[4,3-d]pyrimidin-7-ol

A solution of 108 g (0.05 mol) of 1-ethyl-3-methyl-4-nitro-pyrazole-5-carbonyl chloride [J. Med. Chem. 16 1346 (1973)] in 100 ml of acetone is added at a fast droprate to 450 ml cold concentrated ammonium hydroxide with stirring. After one hour, the mixture is filtered; the product is washed with water to give 94 g (95%) of 1-ethyl-3-methyl-4-nitropyrazole-5-carboxamide, mp 175°–177° C.

A mixture of 20 g (0.1 mol) of the above amide in 150 ml of ethanol and 30 ml of water containing 3 ml of conc. HCl is stirred under reflux with 25 g of iron powder for three hours and filtered warm using filter-cell. The filtrate is evaporated in vacuo to yield a pink solid, mp 143°–145° C. (from ethyl acetate-pet. ether) of 4-amino-1-ethyl-3-methylpyrazole-5-carboxamide. The reaction of this aminopyrazole with 18 ml acetic anhydride in 250 ml of methylene dichloride gives 18.5 g of N-(1-ethyl-5-carboxamido 3-methylpyrazol-4-yl)acetamide, mp 248°–250° C.

The above compound (18.5 g, 0.088 mol) is stirred in 120 ml of 1N sodium hydroxide at 90° C. for two hours. The resulting solution is cooled and acidified with 10 ml of glacial acetic acid. The solid is collected by filtering and washed with water to give 14 g (83%) of 1-ethyl-3,5-dimethyl-1H-pyrazolo[4,3-d]pyrimidin-7-ol, mp 220°–223° C.

EXAMPLE 16-b 7,8-Dihydro-1-ethyl-3,5-dimethyl-1H-imidazo[1,2-c]pyrazolo[3,4-e]pyrimidine A solution of 12 g (0.057 mol) of 7-chloro-3,5-dimethyl-1-ethyl-1H-pyrazolo[4,3-d]pyrimidine in 150 ml of methylene dichloride is treated with 12 g (0.2 mol) of 2-aminoethanol and 8 ml of triethyamine and stirred at room temperature 48 hours. The mixture is filtered to give 7.6 g (56%) of 2-[1-ethyl-3,5-dimethyl-1H-pyrazolo[4,3-d]pyrimidin-7-yl]aminoethanol, mp 181°–183° C. from ethyl acetate.

The above aminoalcohol (6 g, 0.025 mol) is refluxed 1.5 hours in 50 ml of phosphorus oxychloride and the solution is evaporated in vacuo. The residue is dissolved in 75 ml of water and made basic with sodium carbonate to precipitate 4.5 g (81%) of title compound, mp 166°–168° C. from toluene-pet. ether.

EXAMPLE 17

7,8-Dihydro-1-ethyl-3,5,8-trimethyl-1H-imidazo[1,2-c]pyrazolo[3,4-e]pyrimidine

A solution of 4.2 g (0.02 mol) of 7-chloro-3,5-dimethyl-1-ethyl-1H-pyrazolo[4,3-d]pyrimidine (Ex. 16), 3 ml of triethylamine and 5 ml of 2-methylaziridine in 100 ml of methylene dichloride is allowed to stand at room temperature 20 hours. The solution is washed with saturated sodium bicarbonate solution, dried (MgSO₄), and evaporated in vacuo to give 4 g of 1-ethyl-3,5-dimethyl-7-(2-methylaziridinyl)pyrazolo[4,3-d]pyrimidine as an oil, characterized by IR and NMR. The aziridine (4 g, 0.017 mol) in 40 ml of acetone is refluxed 1.5 hours with 3 g (0.02 mol) of sodium iodide. The solution is evaporated in vacuo. The residue is partitioned in 100 ml of methylene dichloride and 30 ml of 20% sodium carbonate solution. The organic layer is separated, dried over magnesium sulfate, and the solvent is evaporated in vacuo to give 2.8 g (71%) of the title compound, mp 145°–147° C. from ethyl acetate-pet ether.

EXAMPLE 18

1,5-Diethyl-7,8-dihydro-3,8-dimethyl-1H-imidazo[1,2-c]pyrazolo[3,4-e]pyrimidine

A mixture of 14 g (0.068 mol) of 1,5-diethyl-3-methyl-1H-pyrazolo[4,3-d]pyrimidin-7-ol and 15 g (0.07 mol) of phosphorus pentachloride in 100 ml of phosphorus oxychloride is stirred under reflux 5.5 hours and evaporated in vacuo. The residue is treated with 100 ml of ether and decanted from some tar. The ether solution is evaporated in vacuo and the residue is treated with 100 ml of pet ether and again decanted from some insolubles. The pet ether solution is evaporated in vacuo to give 14 g oil that solidifies on standing.

The above compound, 7-chloro-1,5-diethyl-3-methyl-1H-pyrazolo[4,3-d]pyrimidine (4.4 g, 0.02 mol) is dissolved in 75 ml of methylene dichloride and treated with 4 ml of triethylamine and 4 ml of 2-methylaziridine. After standing at room temperature for 40 hours, the mixture is washed with an aqueous saturated solution of sodium bicarbonate, dried over MgSO₄, and evaporated in vacuo to give 4.4 of 1,5-dimethyl-3-methyl-7-[N-(2-methyl)aziridinyl]-1H-pyrazolo[4,3-d]pyrimidine as an oil, characterized by its NMR spectra.

The above aziridine (4.4 g, 0.018 mol) is heated under reflux in 75 ml acetone with 4 g of sodium iodide for 1.5 hours. The mixture is partitioned in 100 ml methylene dichloride and 25 ml of water. The organic layer is separated, dried over MgSO₄, and evaporated in vacuo to yield 4 g of solid. The product is recrystallized from acetonitrile to give 2.4 g, mp 120° C. of the title compound.

Preparation of
1,5-diethyl-3-methyl-1H-pyrazolo[4,3-d]pyrimidin-7-ol

Treatment of a suspension of 21.8 g (0.13 mol) of 4-amino-1-ethyl-3-methylpyrazole-5-carboxamide (Example 16-a) in 300 ml of methylene dichloride with 13 g (0.14 mol) of propionyl chloride in the presence of 20 ml of triethylamine gives 20 g (69%) of N-[4-(5-carboxamido-1-ethyl-3-methylpyrazolyl)propionamide], mp 229°–231° C. The reaction of 19.5 g (0.087 mol) of this amide with 120 ml of 1N sodium hydroxide at 90° C. for 2.5 hours, followed by acidification with 12 ml of glacial acetic acid gives 16.5 g (92%) of 1,5-diethyl-3-methyl-1H-pyrazolo[4,3-d]pyrimidin-7-ol, mp 192°–194° C.

EXAMPLE 19

7,8-Dihydro-3,5,8-trimethyl-1-n-propyl-1H-imidazo[1,2-c]pyrazolo[3,4-e]pyrimidine A mixture of 9.6 g (0.047 mol) of 3,5-dimethyl-1-n-propyl[4,3-d]pyrimidin-7-ol and 10 g (0.05 mol) of phosphorus pentachloride in 80 ml of phosphorus oxychloride is stirred under reflux 4.5 hours and evaporated in vacuo. The residue is dissolved in methylene dichloride (150 ml) and stirred well with 100 ml of saturated NaHCO₃ solution; the organic solution is separated, dried over MgSO₄, and evaporated in vacuo. The oil is stirred with 50 ml of pet ether, filtered from some insolubles, and evaporated in vacuo to give 9 g (82%) of 7-chloro-3,5-dimethyl-1-n-propyl[4,3-d]pyrimidine as an oil.

The above chloro compound (9 g, 0.04 mol) is dissolved in 150 ml of methylene dichloride and treated at 10° C. with 8 ml of triethylamine and 10 ml of 2-methylaziridine. The mixture is allowed to stand at room temperature 20 hours and then stirred with 100 ml of saturated aqueous NaHCO₃ and evaporated in vacuo to give 8 g (81%) of 3,5-dimethyl-7-[N-(2-methyl)aziridinyl]1-n-propyl-1H-pyrazolo[4,3-d]pyrimidine as an oil, characterized by its IR and NMR spectra.

The above aziridine (8 g, 0.032 mol) is refluxed in 50 ml of acetone with 6 g (0.04 mol) of sodium iodide for 1.5 hours and evaporated in vacuo. The residue is partitioned in 100 ml of methylene chloride and 30 ml of water. The organic layer is separated, dried over MgSO₄, and evaporated in vacuo. The solid is triturated with hexane to give 5.1 g (63%) mp 85°–90° C. of the title compound.

Preparation of
3,5-dimethyl-1-n-propyl-1H-pyrazolo[4,3-d]pyrimidin-7-ol

A solution of 46 g (0.2 mol) of 3-methyl-4-nitro-1-n-propyl-pyrazole-5-carbonyl chloride [J. Med. Chem., 16 1346 (1973)] in 50 ml of acetone is added slowly to 250 ml of cold (5° C.) concentrated ammonium hydroxide. The mixture is filtered to give 33 g (79%) of 3-methyl-4-nitro-1-n-propylpyrazole-5-carboxamide, mp 136°–138° C. The amide (33 g, 0.15 mol) is stirred under reflux in 100 ml of phosphorus oxychloride for 2.5 hours and evaporated in vacuo. The residue is stirred in 250 ml of ice water to give, after filtering, 25.5 g (86%) of 5-cyano-3-methyl-4-nitro-1-n-propylpyrazole. This nitropyrazole (25 g, 0.013 mol) is dissolved in 350 ml of glacial acetic acid and treated at 95° C. portionwise with 12 g iron filings and 20 ml of water. After stirring under reflux three hours the mixture is filtered and the filtrate is concentrated in vacuo. The concentrate is extracted with methylene dichloride and the organic extract is treated with 20 ml of acetic anhydride and refluxed for two hours. The cooled mixure is stirred with saturated aqueous NaHCO₃ solution, the organic layer is dried (MgSO₄), and evaporated in vacuo to give 16.5 g of N-(5-cyano-3-methyl-1-n-propylpyrazol-4-yl)acetamide, mp 129°–131° C.

The above acetamide (16 g, 0.085 mol) is added in portions with stirring at 80° C. to a solution prepared by adding 24 ml of 30% hydrogen peroxide to 200 ml water containing 6 g (0.015 mol) of sodium hydroxide. After stirring at 80° C. for five hours, the mixture is cooled, acidified with acetic acid, and filtered to give 11.6 g (66%) of the title compound, mp 196°–198° C.

EXAMPLE 20

7,8-Dihydro-3,5,8-trimethyl-1-(2,2,2-trifluoroethyl)-1H-imidazo[1,2-c]pyrazolo[3,4-e]pyrimidine A mixture of 10 g (0.04 mol) of 7,8-dihydro-3,5-dimethyl-1-(2,2,2-trifluoroethyl)-1H-pyrazolo[4,3-d]pyrimidin-7-one and 9 g (0.045 mol) of phosphorus pentachloride in 100 ml of phosphorus oxychloride is stirred under reflux for six hours and evaporated in vacuo. The residue is stirred in 150 ml of ether and decanted from insolubles. The ether solution is evaporated in vacuo, and this residue is treated with 150 ml of pet ether and again the solution is decanted from insolubles. Evaporation of the solution gives 8.5 g of 7-chloro-3,5-dimethyl-1-(2,2,2-trifluoroethyl)-1H-pyrazolo[4,3-d]pyrimidine, mp 70° C.

A solution of 4.6 g (0.0175 mol) of this chloropyrimidine, 3 ml of triethylamine and 3 ml of 2-methylaziridine in 100 ml of methylene dichloride is allowed to stand at room temperature for 40 hours. The solution is washed with a saturated solution of sodium bicarbonate, dried over magnesium sulfate and evaporated to give 3.5 g of 3,5-dimethyl-7-(2-methylaziridinyl)-1-(2,2,2-trifluoroethyl-1H-pyrazolo[4,3-d]pyrimidine as an oil. This oil (3.5 g) is refluxed two hours in 50 ml of acetone with 3 g of sodium iodide and evaporated in vacuo. The residue is treated with 25 ml of water and extracted with methylene dichloride to give 3.5 g of oil. Chromatography of the oil over silica gel in acetonitrile gives 1.3 g of title compound, mp 91°–95° C. from ether.

Preparation of
7,8-dihydro-3,5-dimethyl-1-(2,2,2-trifluoroethyl)-1H-pyrazolo[4,3-d]pyrimidin-7-one A mixture of 100 g (0.35 mol) of the trichloromethanesulfonate ester of 2,2,2-trifluoroethanol [J. Med. Chem. 16 1354 (1973)] and 55 g (0.35 mol) of ethyl 3-methylpyrazole-5-carboxylate is heated at 150°–155° C. for two hours. The cooled (70° C.) melt is poured with stirring into 400 ml of ether, 80 ml of conc. ammonium hydroxide, and 150 g ice. The ether layer is separated and distilled to give 48 g bp 100°–110°/11 mm. The ester is stirred under reflux two hours in 175 ml of ethanol and 40 ml of water containing 14 g of potassium hydroxide and evaporated in vacuo. The residue is dissolved in 60 ml of water and acidified with conc. HCl to give 32 g (72%) of 1-(2,2,2-trifluoroethyl)-3-methylpyrazole-5carboxylic acid, mp 135°–139° C.

The above acid (22 g, 0.11 mol) is added in portions at 70°–90° C. to a stirred acid mixture prepared by adding 30 ml conc. sulfuric acid to 15 ml of 90% nitric acid. After stirring two hours at 95°, the mixture is poured into 75 g of ice. The collected precipitate is dried to give 23 g, 1-(2,2,2-trifluoroethyl)-3-methyl-4-nitropyrazole-5-carboxylic acid, mp 135°–138° C. This nitro acid (23 g, 0.09 mol) is mixed with 21 g (0.1 mol) of phosphorus pentachloride and heated on a steam bath for 2.5 hr, filtered, and evaporated in vacuo to give 20 g of 1-(2,2,2-trifluoroethyl)-3-methyl-4-nitropyrazole-5-carbonyl chloride as an oil. The acid chloride (20 g) in 30 ml of acetone is added dropwise to 130 ml cold concentrated ammonium hydroxide and the mixture is filtered after stirring one hour to give 16 g of 3-methyl-4-nitro-1-(2,2,2-trifluoroethyl)-5-pyrazolecarboxamide, mp 205°–207° C. from ethyl acetate.

A mixture of 16 g (0.063 mol) of 3-methyl-4-nitro-1-(2,2,2-trifluoroethyl)-5-pyrazolecarboxamide and 18 g of iron powder in 120 ml of ethanol, 2 ml of concentrated hydrochloric acid and 18 ml of water is stirred under reflux for three hours. The mixture is filtered hot and the filtrate is evaporated in vacuo. A sample of the amine melts at 170°–172° C. from ethyl acetate. The remainder of the amine product is stirred in 100 ml of methylene dichloride and 12 ml of acetic anhydride is added. After stirring overnight, the mixture is diluted with pet ether and filtered to give 14.5 g (87%) of product, mp 250°–252° C.

This amide (14.4 g, 0.054 mol) is stirred in 100 ml of 1N sodium hydroxide for three hours at 80°–90° C. The solution is cooled and acidified with acetic acid to precipitate 12.4 g (92%) of 7,8-dihydro-3,5-dimethyl-1-(2,2,2-trifluoroethyl)-1H-pyrazolo[4,3-d]pyrimidin-7-one, mp 276°–279° C.

EXAMPLE 21

1,3,5,8-Tetramethyl-1H-imidazo[1,2-c]pyrazolo[3,4-e]pyrimidine

A mixture of 2.4 g (0.011 mol) of 7,8-dihydro-1,3,5,8-tetramethyl-1H-imidazo[1,2-c]pyrazolo[3,4-e]pyrimidine and 5.6 g (0.022 mol) of chloranil in 400 ml of xylene is stirred under reflux four hours. The warm mixture is extracted with two 150 ml portions of 1N sodium hydroxide. The organic layer is separated, filtered, dried over MgSO₄, and evaporated in vacuo. The solid residue is stirred in ether to give 1.2 g (50%) of the title compound, mp 198°–200°.

EXAMPLE 22

1,3,5,7,8-Pentamethyl-1H-imidazo[1,2-c]pyrazolo[3,4-e]pyrimidine

A mixture of 9.5 g (0.05 mol) of 7-chloro-1,3,5-trimethyl-1H-pyrazolo[4,3-d]pyrimidine (Example 3), 10 g (0.075 mol) of 3-amino-2-butanone, ethylene ketal, and 14 ml of triethylamine in 30 ml of dimethylformamide is stirred at 50°–55° C. for 24 hours. The mixture is evaporated in vacuo, the residue is dissolved in methylene dichloride and washed with ammonium hydroxide solution. The organic layer is dried over MgSO₄ and evaporated in vacuo. The residue is crystallized from pet ether to give 12.6 g (87%) of 1,3,5-trimethyl-N-[1-(2-methyl-1,3-dioxolan-2-yl)ethyl]-1H-pyrazol[4,3-d]pyrimidin-7-amine, mp 101°–103° C.

This compound (10.5 g, 0.036 mol) is warmed in 60 ml of concentrated sulfuric acid on the steam bath for 0.5 hours. The cooled solution is added slowly to a stirred mixture of 150 g ice, 150 ml concentrated NH₄OH, and 400 ml of methylene dichloride. The organic layer is separated and dried over MgSO₄. Evaporation of the solvent gives 2.5 g, mp 170°–173° from acetonitrile or ethyl acetate.

EXAMPLE 23

5,6,7,8-Tetrahydro-5-ethyl-1,3,8-trimethyl-1H-imidazo[1,2-c]pyrazolo[3,4-e]pyrimidine p-Toluenesulfonic acid monohydrate (15.2 g, 0.08 mol) is added in portions with stirring to 6 g (0.08 mol) of 1,2-diaminopropane under nitrogen. To the resulting melt (ca 100° C.) is added in portions 12.6 g (0.076 mol) of 5-cyano-1,3-dimethyl-4-nitropyrazole (mp 93° C.); the mixture is stirred and heated to 120° C. and 25 ml of o-dichlorobenzene is added; stirring is continued at 120°–130° for 0.5 hours then at 160° C. for three hours. The cooled mixture is extracted with 75 ml of 3N HCl. The aqueous extract is made strongly basic with a large excess of concentrated NH₄OH and the mixture is extracted thoroughly with methylene dichloride. Evaporation of the extract gives 14.3 g (84%) of 2-(1,3-dimethyl-4-nitropyrazol-5-yl)-4-methylimidazoline, mp 98°–101°.

The above nitro compound (9 g, 0.04 mol) is reduced by refluxing with 14 g of iron powder in 150 ml 90% ethanol containing 1 ml concentrated HCl for three hours. The mixture is filtered and evaporated to give 7.8 g of 5-(4,5-dihydro-4(or 5)-methyl-1H-imidazol-2-yl)-1,3-dimethyl-1H-pyrazol-4-amine, mp 243°–245° C. as the hydrochloride salt.

The above amine (7.5 g, 0.038 mol) is dissolved in 75 ml of absolute ethanol and refluxed 16 hours with 4.5 g (0.07 mol) of propionaldehyde under nitrogen. The mixture is evaporated in vacuo and the residue is crystallized from acetonitrile to give 1.9 g (22%) of the title compound, mp 186°–188° C., as the dihydrate.

EXAMPLE 24

5-Ethyl-1,3,8-trimethyl-1H-imidazo[1,2-c]pyrazolo[3,4-e]pyrimidine

Manganese dioxide (35 g) is dried by stirring in 250 ml of toluene under reflux with a water separator for one to two hours. 7,8-Dihydro-5-ethyl-1,3,8-trimethyl-1H-imidazo[1,2-c]pyrazolo[3,4-e]pyrimidine (4 g, 0.017 mol) from Example 12 is added, and the mixture is stirred under reflux four hours. The mixture is filtered and the filtrate is concentrated in vacuo. The resulting suspension is diluted with pet ether and filtered to give 2.7 g (68%) of the title compound, mp 182°–183° C.

EXAMPLE 25

1,3,5,8-Tetramethyl-1H-imidazo[1,2-c]pyrazolo[3,4-e]pyrimidine 7,8-Dihydro-1,3,5,8-tetramethyl-1H-imidazo[1,2-c]pyrazolo[3,4-c]pyrimidine (2.4 g, 0.011 mole) is oxidized with 25 g of manganese dioxide in 150 ml of refluxing toluene by the procedure of Example 24 to give 1.2 g (50%) of the title compound, mp 197°–199° C.

I claim:

1. A compound having the structural formula I

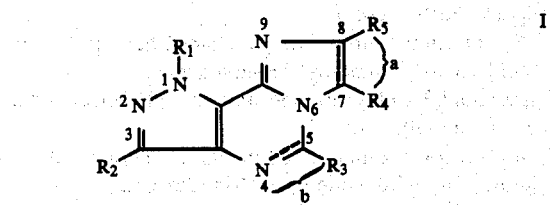

wherein the dashed lines "a" and "b" represent optional double bonds, provided that "a" is not a double bond when "b" is not a double bond; $R_1$, $R_2$, $R_3$, $R_4$, and $R_5$ are H, alkyl of from one to six carbon atoms, or fluorinated alkyl of from one to three carbon atoms; when "a" represents a single bond, $R_4$ may be H/H and $R_5$ is dialkyl each of from one to six carbon atoms or $R_5$ may be H/H and $R_4$ is dialkyl each of from one to six carbon atoms; and the pharmaceutically acceptable salts thereof.

2. A compound defined in claim 1 having the structural formula Ia wherein $R_1$, $R_2$, $R_3$, $R_4$, and $R_5$

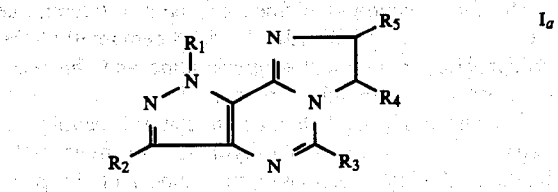

are H, alkyl of from one to six carbon atoms, or fluorinated alkyl of from one to three carbon atoms; $R_4$ may be H/H and $R_5$ is dialkyl each of from one to six carbon atoms or $R_5$ may be H/H and $R_4$ is dialkyl each of from one to six carbon atoms; and the pharmaceutically acceptable salts thereof.

3. A compound defined in claim 1 having the structural formula Ib wherein $R_1$, $R_2$, $R_3$, $R_4$, and $R_5$

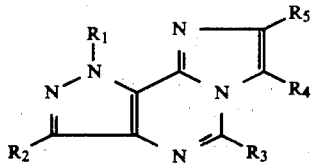

are H, alkyl of from one to six carbon atoms, or fluorinated alkyl of from one to three carbon atoms; and the pharmaceutically acceptable salts thereof.

4. A compound defined in claim 1 having the structural formula Ic wherein $R_1$, $R_2$, $R_3$, $R_4$, and $R_5$

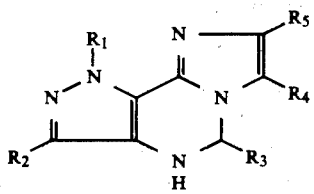

are H, alkyl of from one to six carbon atoms, or fluorinated alkyl of from one to three carbon atoms; $R_4$ may be H/H and $R_5$ is dialkyl of from one to six carbon atoms or $R_5$ may be H/H and $R_4$ is dialkyl each of from one to six carbon atoms; and the pharmaceutically acceptable salts thereof.

5. The compound defined in claim 1 having the name 7,8-dihydro-1,3-dimethyl-1H-imidazo[1,2-c]pyrazolo[3,4-e]pyrimidine and the pharmaceutically acceptable salts thereof.

6. The compound defined in claim 1 having the name 7,8-dihydro-1,3,8-trimethyl-1H-imidazo[1,2-c]pyrazolo[3,4-e]pyrimidine and the pharmaceutically acceptable salts thereof.

7. The compound defined in claim 1 having the name 7,8-dihydro-1,3,5,8-tetramethyl-1H-imidazo[1,2-c]pyrazolo[3,4-e]pyrimidine and the pharmaceutically acceptable salts thereof.

8. The compound defined in claim 1 having the name 7,8-dihydro-1,3,5,8-tetramethyl-1H-imidazo[1,2-c]pyrazolo[3,4-e]pyrimidine (S-form) and the pharmaceutically acceptable salts thereof.

9. The compound defined in claim 1 having the name 7,8-dihydro-1,3,5-trimethyl-1H-imidazo[1,2-c]pyrazolo[3,4-e]pyrimidine (R-form) and the pharmaceutically acceptable salts thereof.

10. The compound defined in claim 1 having the name 7,8-dihydro-1,3,5,7,8-pentamethyl-1H-imidazo[1,2-c]pyrazolo[3,4-e]pyrimidine and the pharmaceutically acceptable salts thereof.

11. The compound defined in claim 1 having the name 8-ethyl-7,8-dihydro-1,3,5-trimethyl-1H-imidazo[1,2-c]pyrazolo[3,4-e]pyrimidine and the pharmaceutically acceptable salts thereof.

12. The compound defined in claim 1 having the name 7,8-dihydro-8-isopropyl-1,3,5-trimethyl-1H-imidazo[1,2-c]pyrazolo[3,4-e]pyrimidine dihydrochloride (S-form) and the pharmaceutically acceptable salts thereof.

13. The compound defined in claim 1 having the name 7,8-dihydro-1,3,5,7,7-pentamethyl-1H-imidazo[1,2-c]pyrazolo[3,4-e]pyrimidine and the pharmaceutically acceptable salts thereof.

14. The compound defined in claim 1 having the name 7,8-dihydro-1,3,5,8,8-pentamethyl-1H-imidazo[1,2-c]pyrazolo[3,4-e]pyrimidine and the pharmaceutically acceptable salts thereof.

15. The compound defined in claim 1 having the name 5-ethyl-7,8-dihydro-1,3-dimethyl-1H-imidazo[1,2-c]pyrazolo[3,4-e]pyrimidine and the pharmaceutically acceptable salts thereof.

16. The compound defined in claim 1 having the name 7,8-dihydro-5-ethyl-1,3,8-trimethyl-1H-imidazo[1,2-c]pyrazolo[3,4-e]pyrimidine and the pharmaceutically acceptable salts thereof.

17. The compound defined in claim 1 having the name 7,8-dihydro-5-ethyl-1,3,7-trimethyl-1H-imidazo[1,2-c]pyrazolo[3,4-e]pyrimidine and the pharmaceutically acceptable salts thereof.

18. The compound defined in claim 1 having the name 7,8-dihydro-5-isopropyl-1,3,8-trimethyl-1H-imidazo[1,2-c]pyrazolo[3,4-e]pyrimidine and the pharmaceutically acceptable salts thereof.

19. The compound defined in claim 1 having the name 1-ethyl-7,8-dihydro-3,5-dimethyl-1H-imidazo[1,2-c]pyrazolo[3,4-e]pyrimidine and the pharmaceutically acceptable salts thereof.

20. The compound defined in claim 1 having the name 7,8-dihydro-1-ethyl-3,5,8-trimethyl-1H-imidazo[1,2-c]pyrazolo[3,4-e]pyrimidine and the pharmaceutically acceptable salts thereof.

21. The compound defined in claim 1 having the name 1,5-diethyl-7,8-dihydro-3,8-dimethyl-1H-imidazo[1,2-c]pyrazolo[3,4-e]pyrimidine and the pharmaceutically acceptable salts thereof.

22. The compound defined in claim 1 having the name 7,8-dihydro-3,5,8-trimethyl-1-n-propyl-1H-imidazo[1,2-c]pyrazolo[3,4-e]pyrimidine and the pharmaceutically acceptable salts thereof.

23. The compound defined in claim 1 having the name 7,8-dihydro-3,5,8-trimethyl-1-(2,2,2-trifluoroethyl)1H-imidazo[1,2-c]pyrazolo[3,4-e]pyrimidine and the pharmaceutically acceptable salts thereof.

24. The compound defined in claim 1 having the name 1,3,5,8-tetramethyl-1H-imidazo[1,2-c]pyrazolo[3,4-e]pyrimidine and the pharmaceutically acceptable salts thereof.

25. The compound defined in claim 1 having the name 1,3,5,7,8-pentamethyl-1H-imidazo[1,2-c]pyrazolo[3,4-e]pyrimidine and the pharmaceutically acceptable salts thereof.

26. The compound defined in claim 1 having the name 5,6,7,8-tetrahydro-5-ethyl-1,3,8-trimethyl-1H-imidazo[1,2-c]pyrazolo[3,4-e]pyrimidine and the pharmaceutically acceptable salts thereof.

27. The compound defined in claim 1 having the name 5-ethyl-1,3,8-trimethyl-1H-imidazo[1,2-c]pyrazolo[3,4-e]pyrimidine and the pharmaceutically acceptable salts thereof.

* * * * *

UNITED STATES PATENT AND TRADEMARK OFFICE
CERTIFICATE OF CORRECTION

PATENT NO. : 4,469,868
DATED : SEPTEMBER 4, 1984
INVENTOR(S) : HORACE A. DEWALD

It is certified that error appears in the above—identified patent and that said Letters Patent is hereby corrected as shown below:

COLUMN 27, CLAIM 4, FORMULA Ic, THAT PORTION OF THE FORMULA READING

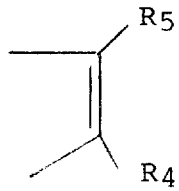      SHOULD READ      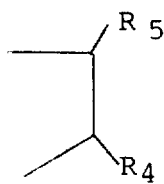

Signed and Sealed this

Fifth Day of March 1985

[SEAL]

*Attest:*

DONALD J. QUIGG

*Attesting Officer*     *Acting Commissioner of Patents and Trademarks*